United States Patent [19]

Burk

[11] Patent Number: 5,202,493
[45] Date of Patent: Apr. 13, 1993

[54] CHIRAL TRIDENTATE BIS(PHOSPHOLANE) LIGANDS

[75] Inventor: Mark J. Burk, Hockessin, Del.

[73] Assignee: E. I. Du Pont de Nemours and Company, Wilmington, Del.

[21] Appl. No.: 691,954

[22] Filed: Apr. 26, 1991

[51] Int. Cl.$^5$ .............................. C07F 9/02; C07F 9/00
[52] U.S. Cl. ..................................... 568/12; 568/13; 568/16; 556/13; 556/14; 556/20; 556/64
[58] Field of Search ................. 556/13, 19, 20, 21, 556/14, 64, 70; 568/579, 12, 10, 13, 15, 16

[56] References Cited

U.S. PATENT DOCUMENTS

| | | | |
|---|---|---|---|
| 4,391,756 | 7/1983 | Kuch et al. | 556/21 X |
| 4,394,322 | 7/1983 | Beach et al. | 556/21 X |
| 4,415,500 | 11/1983 | Manassen et al. | 556/21 X |
| 5,008,457 | 4/1991 | Burk | 568/12 |
| 5,021,131 | 6/1991 | Burk | 204/59 |

OTHER PUBLICATIONS

U.S. Pat. Ser. No. 7644526, filed Jan. 1991 to Burk.
U.S. Pat. Ser. No. 7725121 filed Jul. 1991 to Burk.
Brunner et al., *J. Org. Chem.*, 328, 71–80 (1987).
S. R. Wilson and A. Pasternak, *Synlett*, Apr. 1990, 199-200.
M. J. Burk et al., *Organomteallics*, 9, 2653-2655 (1990).
M. J. Burk et al., *Angewandte Chemie,* Int'l Ed. in English, 29, 1462-1464 (1990).

*Primary Examiner*—Arthur C. Prescott
*Attorney, Agent, or Firm*—Kathleen W. Geiger

[57] ABSTRACT

Chiral tridentate bis(phospholanes) which coordinate as ligands in a meridinal fashion on an octahedral metal or which coordinate in square-planar environments are provided with a method for their preparation.

26 Claims, No Drawings

CHIRAL TRIDENTATE BIS(PHOSPHOLANE) LIGANDS

FIELD OF THE INVENTION

The invention relates to novel chiral tridentate bis(phospholanes) and a method for their preparation. The compounds, when complexed with transition metals, are efficient catalysts for carrying out enantioselective reactions.

BACKGROUND OF THE INVENTION

The development of novel catalytic systems exhibiting unique reactivity and high enantioselectivity requires the synthesis of chiral ligands for transition metals. Generally, some of the most successful chiral ligands have been chelating phosphines possessing a $C_2$ symmetry axis.

Many of the chiral phosphines known in the art have at least two aryl substituents on the phosphorous, rendering that center relatively electron-poor. The mechanism of asymmetric induction using these phosphines has been linked to the proper conformational relationship between the phenyl groups on the phosphorous centers.

More recently, chiral phosphines having relatively electron-rich phosphorus centers have been reported Brunner et al., Journal of Organometallic Chemistry, Vol. 328, PP 71-80 (1987) teach 3,4-disubstituted phospholanes derived from tartaric acid having chloro, methoxy, or dimethylamino substituents. These were complexed with manganese and rhodium and used as catalysts in the hydrogenation of alpha-N-acetamidocinnamic acid. Relatively low optical yields of (S)-N-acetylphenylalanine of from 6.6% enantiomeric excess to 16.8% enantiomeric excess were obtained.

S. R. Wilson and A. Pasternak, Synlett, April, 1990, pp 199-200 describe the preparation of (2R,5R)-1-phenyl-2,5-dimethylphospholane and its use in an enantioselective Staudinger reaction (reduction of azides with phosphines). Here the chiral (2R,5R)-1-phenyl-2,5-dimethylphospholane is used as a stoichiometric reactant, not as a catalyst.

M. J. Burk et al, Organometallics, Vol 9, pp 2653-2655 (1990) describe a series of mono and bidentate 2,5disubstituted phospholanes and demonstrate their use as ligands in asymmetric catalysis. Rhodium complexes bearing the disclosed phosphine ligands were prepared and tested as catalyst precursors for the enantioselective hydrogenation of unsaturated substrates. The phosphorous atoms in the disclosed bis(phospholanes) are linked by two- or three- carbon methylene bridges. There is no indication nor suggestion that these bridges linking the phosphorus atoms might contain heteroatoms. There is no indication nor suggestion that a bis(phospholane) where the bridge linking the phosphorus atoms contains heteroatoms would be able to complex transition metals in a tridentate fashion.

M. J. Burk et al, Angewandte Chemie, International Edition in English, Vol 29, pp 1462-1464 (1990) disclose tris(phospholane) tridentate ligands with $C_3$ symmetry. There is no indication nor suggestion that a bis(phospholane) where the bridge linking the phosphorus atoms contains heteroatoms would be able to complex transition metals in a tridentate fashion.

U.S. Pat. No. 5,008,457 issued Apr. 16, 1991, discloses mono, bidentate and tridentate phospholanes useful as transition metal ligands in assymetric catalysis and processes for their preparation as in the above two Burk et al. references.

A continuing need exists for transition metal complexes providing high levels of stereochemical control and asymmetric induction in stoichiometric and catalytic transformations. There are no known examples of chiral tridentate phospholane ligands which can coordinate in a meridinal fashion on an octahedral metal or which coordinate in square-planar environments. The tris(phospholanes) of Burk et al., supra, are tridentate ligands, but cannot coordinate in this fashion.

A need also exists for efficient synthetic routes for the preparation of chiral ligands having a high degree of enantiomeric purity for transition metal catalysts.

It is therefore an object of the present invention to provide novel tridentate bis(phospholane) compounds as ligands for transition metals.

It is a further object of the present invention to provide tridentate bis(phospholanes) which coordinate in a meridinal fashion on an octahedral metal or which coordinate in square-planar environments.

It is a further object of the present invention to provide transition metal catalysts which provide high levels of stereochemical control in reactions.

It is a further object of the present invention to provide transition metal catalysts which result in high levels of asymmetric induction in hydrogenation reactions.

It is a further object of the present invention to provide efficient synthetic routes for the preparation of these bis(phospholane) compounds.

SUMMARY OF THE INVENTION

This invention comprises tridentate bis(phospholanes) of the structure

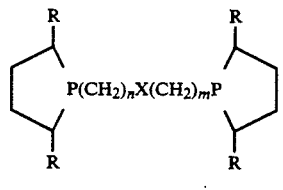

wherein:

R is a radical comprising alkyl, fluoroalkyl or perfluoroalkyl, each containing up to about 8 carbon atoms; aryl; substituted aryl; aralkyl; ring-substituted aralkyl; or $-CR'_2(CR'_2)_qX(CR'_2)_pR'$ wherein q and p are each integers, the same or different, ranging from 1 to about 8; X is as defined below; and R' is H; F; aryl; or alkyl, fluoroalkyl or perfluoroalkyl, each containing up to about 8 carbon atoms;

n and m are each integers, the same or different, ranging from 1 to about 8; and X comprises O, S, NR'', PR'', AsR'', SbR'', divalent aryl, divalent fused aryl, divalent 6-membered ring heterocyclic group, divalent 5-membered ring heterocyclic group, or divalent fused heterocyclic group, wherein R'' is hydrogen; alkyl, fluoroalkyl or perfluoroalkyl, each containing up to about 8 carbon atoms; aryl; substituted aryl; aralkyl; ring-substituted aralkyl; or $CR'_2(CR'_2)_qZ(CR'_2)_pR'$ wherein Z is O, S, NR', PR', AsR' or SbR', and R', q, and p are as defined above.

This invention also provides a process for the preparation of a compound represented by the following formula:

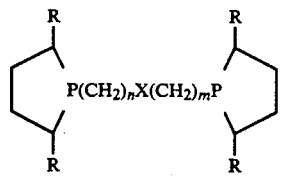

wherein:

R is a radical comprising alkyl, fluoroalkyl or perfluoroalkyl, each containing up to about 8 carbon atoms; aryl; substituted aryl; aralkyl; ring-substituted aralkyl; or —CR'$_2$(CR'$_2$)$_q$X(CR'$_2$)$_p$R' wherein q and p are each integers, the same or different, ranging from 1 to about 8; X is as defined below; and R' is H; F; aryl; or alkyl, fluoroalkyl or perfluoroalkyl, each containing up to about 9 carbon atoms;

n and m are each integers, the same or different, ranging from about 1 to about 8; and X comprises O, S, NR'', PR'', AsR'', SbR'', divalent aryl, divalent fused aryl, divalent 6-membered ring heterocyclic group, divalent 5-membered ring heterocyclic group, or divalent fused heterocyclic group, wherein R'' is hydrogen; alkyl, fluoroalkyl or perfluoroalkyl, each containing up to about 8 carbon atoms; aryl; substituted aryl; aralkyl; ring-substituted aralkyl; or CR'$_2$(CR'$_2$)$_q$Z(CR'$_2$)$_p$R' wherein Z is O, S, NR', PR', AsR', or SbR', and R', q, and p are as defined above, comprising reacting an optically active trans-2,5-disubstituted lithium phospholanide with a compound of the structure Y(CH$_2$)$_n$X(CH$_2$)$_m$Y wherein X, n and m are defined as above, and Y is a leaving group, to yield the desired compound as defined above.

This invention further comprises a process for preparation of the above defined compound when X is PR'' wherein R'' is defined as above comprising reacting an optically active trans-2,5-disubstituted lithium phospholanide with a divinylphosphine of the formula R''P(CH=CH$_2$)$_2$ wherein R'' is defined as above.

This invention further comprises complexes of the structure

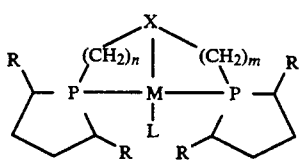

wherein
X, R, m and n are defined as above;
M is a transition metal; and
L is a ligand.

This invention further provides a method for catalyzing a hydrogenation reaction resulting in high levels of enantiomeric excess comprising contacting hydrogen with an olefin, imine, or carbonyl group in the presence of a catalytic amount of the above defined complex.

DETAILED DESCRIPTION OF THE INVENTION

Polydentate phosphine ligands have attracted considerable recent interest, particularly with respect to potential utility in homogeneous catalysis. The versatile yet well-defined electron donor set and rigid chelating nature of these ligands can provide substantial control on the coordination number, electronic properties, and stereochemistry of attached metals. Furthemore, novel systems possessing high order symmetry (i.e., C$_3$- and C$_4$-symmetry) are accessible through the proper introduction of chirality into polydentate phosphine ligands The purpose of the present invention is to provide novel chiral tridentate bis(phospholane) ligands as well as a method for their preparation. These novel chiral tridentate bis(phospholane) ligands are capable of, and are often restricted to, binding transition metals in specific coordination modes (i.e., meridinal vs facial). The present invention provides examples of chiral tridentate phospholane ligands which coordinate in a meridinal fashion on an octahedral metal, or which coordinate in square-planar environments.

The peralkylated nature of these compounds renders the phosphorus center electron-rich. Transition metal complexes containing these ligands demonstrate a high level of enantioselective control and asymmetric induction in the catalyzed hydrogenation of unsaturated substrates, such as olefins, imines or carbonyl groups. The close proximity of the chirality to the metal center of the complex results in an increase of asymmetric induction achieved.

This invention also provides an efficient stereospecific process for the preparation of the novel chiral tridentate bis(phospholanes). The availability of optically active 1,4-diols with a high degree of enantiomeric purity permits preparation of optically active tridentate bis(phospholanes) with a high degree of enantiomeric purity.

For the purpose of this application, a "compound with a high degree of enantiomeric purity", or a "compound of high enantiomeric purity" means a compound that exhibits optical activity to the extent of greater than or equal to about 90%, preferably, greater than or equal to about 95% enantiomeric excess (abbreviated ee).

Enantiomeric excess is defined as the ratio (%R−%S)/(%R+%S), where %R is the percentage of R enantiomer and %S is the percentage of S enantiomer in a sample of optically active compound.

This invention comprises tridentate bis(phospholanes) of the structure

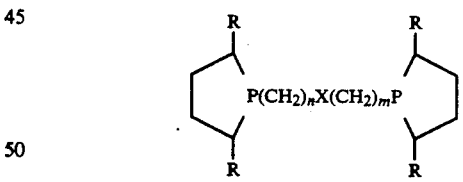

wherein:

R is a radical comprising alkyl, fluoroalkyl or perfluoroalkyl, each containing up to about 8 carbon atoms; aryl; substituted aryl; aralkyl; ring-substituted aralkyl; or —CR'$_2$(CR'$_2$)$_q$X(CR'$_2$)$_p$R' wherein q and p are each integers, the same or different, ranging from 1 to about 8, X is as defined below, and R' is H; F; aryl; or alkyl, fluoroalkyl or perfluoroalkyl, each containing up to about 8 carbon atoms;

n and m are each integers, the same or different, ranging from about 1 to about 8; and X is O, S, NR'', PR'', AsR'', SbR'', divalent aryl, divalent fused aryl, divalent 6-membered ring heterocyclic group, divalent 5-membered ring heterocyclic group, or divalent fused heterocyclic group, wherein R" is hydrogen; alkyl, fluoroalkyl or perfluoroalkyl, each containing up to about 8 carbon atoms; aryl; substituted aryl; aralkyl; ring-substituted aralkyl; or $CR'_2(CR'_2)_qZ(CR'_2)_pR'$ wherein Z is O, S, NR', PR', AsR', or SbR', and R', p, and q are as defined above.

Suitable divalent aryls or fused aryls for use as X herein include but are not limited to those derived from the parent compound: benzene, anthracene, fluorene. Suitable divalent 6-membered ring heterocyclic groups for use as X herein include, but are not limited to, those derived from the parent heterocyclic compound: pyridine, pyran, thiopyran, diazine, triazine, oxazine, isoxazine, oxathiazine, or oxadiazine. Suitable divalent 5-membered ring heterocyclic groups for use herein as X include, but are not limited to, those derived from the parent heterocyclic compound: furan, thiophene, pyrrole, tetrahydrofuran, tetrahydrothiophene, pyrrolidine, arsole or phosphole. Suitable fused heterocyclic groups for use herein include, but are not limited to, those derived from the parent heterocyclic compound: bipyridine, carbazole, benzofuran, indole, benzpyrazole, benzopyran, benzopyronone or benzodiazine.

Preferred are chiral tridentate bis(trans-2,5disubstituted phospholane) compounds of the above structure wherein R is $C_1$ to $C_6$ alkyl, n and m are both from 1 to about 3, and X is NH, P-phenyl, or O. Most preferred are those compounds wherein R is methyl, n and m are both equal to 2, and X is NH, P-phenyl, or O.

The present invention further comprises transition metal complexes of these tridentate bis(phospholanes) of the structure

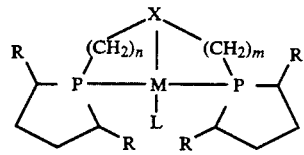

wherein:

R is a radical comprising alkyl, fluoroalkyl or perfluoroalkyl, each containing up to about 8 carbon atoms; aryl; substituted aryl; aralkyl; ring-substituted aralkyl; or —$CR'_2(CR'_2)_qX(CR'_2)_pR'$ wherein q and p are each integers, the same or different, ranging from 1 to about 8, X is as defined below, and R' is H; F; aryl; or alkyl, fluoroalkyl or perfluoroalkyl, each containing up to about 8 carbon atoms;

n and m are each integers, the same or different, ranging from about 1 to about 8; X is O, S, NR", PR", AsR", SbR", divalent aryl, divalent fused aryl, divalent 6-membered ring heterocyclic group, divalent 5-membered ring heterocyclic group, or divalent fused heterocyclic group, wherein R" is hydrogen; alkyl, fluoroalkyl or perfluoroalkyl, each containing up to about 8 carbon atoms; aryl; substituted aryl; aralkyl; ring-substituted aralkyl; or $CR'_2(CR'_2)_qZ(CR'_2)_pR'$ wherein Z is O, S, NR', PR', AsR', or SbR', and R', p, and q are as defined above;

M is a transition metal; and,

L is a ligand.

M can be any of the transition metals of Groups 3 through 12 of the periodic table, plus the lanthanides and actinides. Due to the electron-rich nature of the phospholane compounds they generally coordinate best with the transition metals of Groups 4 through 10. Such complexes are formed by methods known in the art.

L, a ligand, may be a halide; alkyl; aryl; unsaturated hydrocarbyl including but not limited to olefin, diolefin such as cyclooctadiene or norbornadiene or alkyne; acetate; alkoxide; amide; hydride; sulfide; phosphine; carbon monoxide; amine; ether; hydroxide; oxo; imido; or acetylacetonate groups. When the complex has a negative charge, a countercation is required. Examples include ammonium, tetraalkylammonium, sodium, potassium or lithium. When the complex has a positive charge, a counteranion is required. Suitable examples of counteranions are tetrafluoroborate, hexafluoroantimonate or chloride.

Preferred transition metal complexes of the above structure are those wherein R is a lower alkyl of $C_1$ to $C_6$ alkyl; n and m are both equal to 1 to 3; X is NH, P-phenyl, or O; M is a transition metal of Groups 4 through 10; and L is a ligand chosen from the halide group or cyclooctadienyl group with an appropriate counterion.

Most prefered are those complexes where R is methyl; n and m are both equal to 2; X is NH, P-phenyl, or O; M is rhodium; and L is chloride or 1,5-cyclooctadiene with chloride or hexafluoroantimonate counteranions.

Another aspect of the present invention comprises processes for the preparation of the chiral tridentate bis(phospholanes). These compounds are prepared with a high degree of enantiomeric purity.

The processes are summarized in the following scheme.

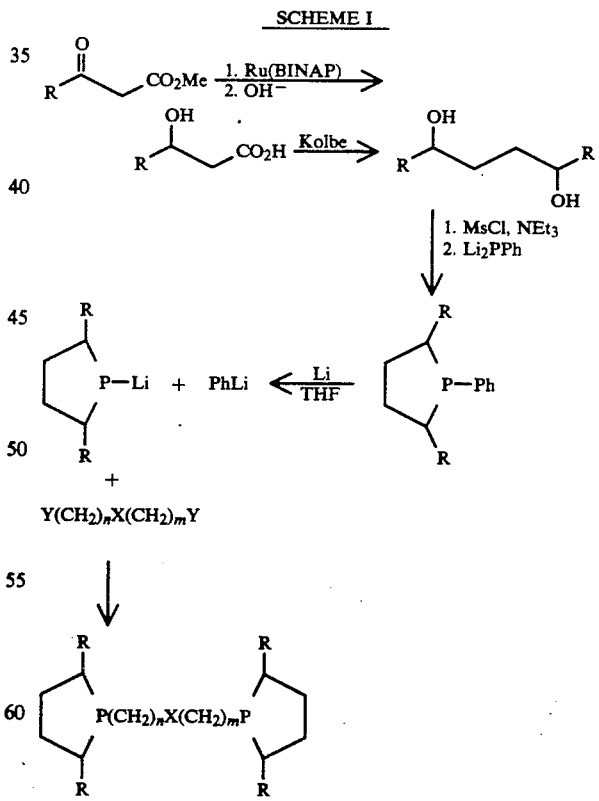

wherein:

R, n, m, and X are as described previously, and Y is a leaving group as described hereinafter in this application.

The first step introduces the desired chirality and utilizes a Ru(BINAP) [Ru-(R)-(+) or (S)-(−)-2,2'-bis-(diphenylphosphino)-1,1'-binaphthyl] catalyst as taught in Noyori et al., J. Amer.Chem. Soc., Vol. 110, p. 629 (1988), which is herein incorporated by reference, for the asymmetric reduction of a β-keto ester to the corresponding β-hydroxy ester. Hydrolysis with a strong base such as KOH provides the free carboxylic acid, which is then subjected to electrochemical Kolbe-coupling to afford a chiral diol. In the Kolbe-coupling reaction a β-hydroxy carboxylic acid of formula RCH(OH)CH$_2$COOH, wherein R is as defined above, is dissolved or suspended in a lower alcohol solvent, together with a catalytic amount of a corresponding alkali metal alkoxide. Electrical current is then passed through the solution or suspenions and the chiral diol product isolated by methods known in the art. The chiral diol is reacted with an alkylsulfonyl chloride, preferably methanesulfonyl chloride, in the presence of a tertiary amine such as triethylamine to form the bis(alkylsulfonate) derivative of the diol. Dilithium phenylphosphide is then added to obtain the chiral 2,5-disubstituted-1-phenylphospholane.

The preparation of chiral tridentate bis(phospholane) compounds of the present invention using 2,5-disubstituted 1-phenylphospholane requires two additional steps. Treatment of the phenylphospholane with lithium with a clean metallic surface results in selective cleavage of the phenyl group and yields a mixture of 2,5-disubstituted lithium phospholanide and phenyllithium. This reaction is conducted in tetrahydrofuran or an equivalent solvent. It is conducted at a temperature range of from about 0° C. to about 40° C., preferably from about 20° C. to about 25° C. This reaction is conducted in the absence of oxygen and water under an inert atmosphere at a pressure of about 1 atm. Preferably the inert atmosphere is argon. Agitation is required since it is a heterogenous reaction with lithium metal. The overall reaction time can range from about 5 to about 30 hours, and typically is from about 10 to about 20 hours. The 2,5-disubstituted lithium phospholanide is used in the processes of the present invention to obtain the desired chiral tridentate bis(phospholane). Suitable 2,5-disubstituted lithium phospholanides for use herein are those of formula

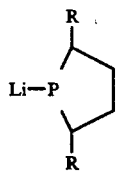

wherein:

R is a radical comprising alkyl, fluoroalkyl or perfluoroalkyl, each containing up to about 8 carbon atoms; aryl; substituted aryl; aralkyl; ring-substituted aralkyl; or —CR'$_2$(CR'$_2$)$_q$X(CR'$_2$)$_p$R' wherein q and p are each integers, the same or different, ranging from about 1 to about 8; R' is H; F; aryl; or alkyl, fluoroalkyl or perfluoroalkyl, each containing up to about 8 carbon atoms; and X is O, S, NR", PR", AsR", SbR", divalent aryl, divalent fused aryl, divalent 6-membered ring heterocyclic group, divalent 5-membered ring heterocyclic group, or divalent fused heterocyclic group, wherein R" is hydrogen; alkyl, fluoroalkyl or perfluoroalkyl, each containing up to about 8 carbon atoms; aryl; substituted aryl; aralkyl; ring-substituted aralkyl; or CR'$_2$(CR'$_2$)$_q$Z(CR'$_2$)$_p$R' wherein Z is O, S, NR', PR', AsR', or SbR'; and R', q, and p are defined as above.

The mixture of 2,5-disubstituted lithium phospholanide and phenyllithium obtained above is then reacted directly with a compound of formula Y(CH$_2$)$_n$X(CH$_2$)$_m$Y, wherein X, n, and m are defined as above in this application and Y is a leaving group, including but not limited to tosylate, halide, triflate, or mesylate, to obtain the desired chiral tridentate bis(phospholane). Other suitable leaving groups are discussed in March, J., Advanced Organic Chemistry, 3rd ed., pp. 310–316, Wiley-Interscience, New York, N.Y. (1985), herein incorporated by reference. A mole ratio of Y(CH$_2$)$_n$X(CH$_2$)$_m$Y to lithium phosphide suitable for use herein is from about 1:2 to about 1:10. Preferred is a mole ratio of 1:2.

For the structure below, an alternate synthetic route can be employed. 2,5-disubstituted lithium phospholanide as defined above is reacted with from about 0.1 to about 0.9 mole equivalents of methanol. The resulting mixture, which corresponds to about 2 to about 10 mole equivalents of phosphorous reagent, is reacted with about 1 mole equivalent of a divinylphosphine of formula R"P(CH=CH$_2$)$_2$ wherein R" is defined as above to yield the tridentate bis(phospholane) shown below

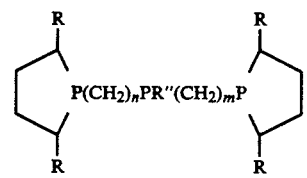

wherein:

R, R", m, and n are as defined above. Preferably R" is phenyl.

These reactions of 2,5-disubstituted lithium phosphide with Y(CH$_2$)$_n$X(CH$_2$)$_m$Y or with methanol and the divinylphosphine are carried out at a temperature range of from about −78° C. to about 40° C., preferably at from about 0° C. to about 25° C. in tetrahydrofuran solvent. An inert atmosphere is employed, preferably argon or nitrogen at about 1 atm. pressure. The reaction mixture is agitated. The overall reaction time for these reactions is from about 0.5 to about 1 hour. The desired product is isolated using methods well known in the art such as distillation, crystallization, evaporation of solvent, filtration, chromotography and the like.

The compounds of the present invention are useful as ligands for transition metal complexes which coordinate in a meridinal fashion on an octahederal metal or which coordinate in square-planar environments. The processes of the present invention are useful in the preparation of these compounds. The complexes of the present invention are useful as transition metal catalysts which provide high levels of stereochemical control in reactions, and which result in high levels of asymmetric induction in hydrogenation reactions.

The following examples illustrate the present invention but are not intended to limit it in any manner.

GENERAL PROCEDURES

General Procedures. All reactions and manipulations were performed in a nitrogen-filled Vacuum Atmospheres Dri-Lab glovebox or using standard Schlenk techniques. Benzene, toluene, diethyl ether (Et$_2$O), tetrahydrofuran (THF), glyme, hexane, and pentane were distilled from sodium-benzophenone ketyl under nitrogen. Acetonitrile (CH$_3$CN) and methylene chloride (CH$_2$Cl$_2$) were distilled from CaH$_2$. Methanol (MeOH) was distilled from Mg(OMe)$_2$.

Melting points were determined using a Mel-Temp apparatus in capillaries sealed under nitrogen and are uncorrected. HPLC analyses were performed using a Hewlett Packard Model HP 1090 LC interfaced to a HP 9000 Series 300 computer workstation. Optical Rotations were obtained using a Perkin Elmer Model 241 MC Polarimeter. NMR spectra were obtained on Nicolet NT-360 wide-bore (360 MHz $^1$H, 146 MHz $^{31}$P), Nicolet NMC-300 wide-bore (300 MHz $^1$H, 120.5 MHz $^{31}$P, 75.5 MHz $^{13}$C) and Nicolet QM-300 narrow-bore (300 MHz $^1$H) spectrometers. $^{13}$C and $^{31}$P NMR chemical shifts are positive downfield (and negative upfield) from external Me$_4$Si and 85% H$_3$PO$_4$, respectively. IR spectra were recorded on a Nicolet 5DXB FT-IR spectrometer. Elemental analyses were performed by Oneida Research Services, Inc., Whitesboro, N.Y., Schwarzkopf Microanalytical Laboratory, Inc., Woodside, N.Y., or Pascher Mikroanalytisches Labor, Remagen-Bandorf (FRG).

Preparation of chiral β-hydroxy esters. The preparation of chiral β-hydroxy esters used in the diol syntheses was carried out as described by Noyori and coworkers who have reported the asymmetric reduction of β-keto esters using a ruthenium catalyst bearing the chiral phosphine ligand BINAP (both enantiomers commercially available from Strem Chemicals). All keto ester reductions were conducted on a 300 g scale in Hasteloy steel autoclave vessels in a MeOH/CH$_2$Cl$_2$ (300 mL/300mL) solvent mixture. The reactions were allowed to proceed at constant H$_2$ pressure (1500 psi) for 48 h at 25° C. Complete conversion of the β-keto ester substrates was observed in all cases and the products were simply distilled from the crude reaction mixture. Consistent with the results of Noyori et al., all products were determined >99% enantiomerically pure.

EXAMPLE 1 a) Preparation of chiral β-hydroxy acids. A mixture of (3R)-methyl 3-hydroxypentanoate (290 g, 2.2 mol) in water (200 mL) and ethanol (200 mL) was cooled to 0° C. To this cold solution was added a solution of KOH (185 g, 3.3 mol) in water (1L). The reaction was then allowed to stir at 25° C. for 48 h. The resulting solution was concentrated to ca. 500 mL and acidified (conc. HCl) until a pH of 1 was reached. The precipitated salts were filtered and the filtrate was subjected to continuous liquid/liquid extraction with diethyl ether (1L) for 24 h. The diethyl ether was removed on a rotovap to afford the product β-hydroxy acid as a colorless oil (250 g, 97%). The crude product was sufficiently pure to use in the next step (Kolbe-coupling).

b) Preparation of (2R, 5R)-2.5-hexanediol. A 1000 mL jacketed reaction vessel is charged with (3R)-3-hydroxybutyric acid (52.0 g, 0.5 mol), methanol (390 mL) and sodium methoxide (110 mL of a 0.5N solution in methanol, 0.055 mol), and the mixture (pH=5.38) was cooled to 0° C. with a circulating bath. The electrode configuration used consists of a Pt foil anode (20 cm$^2$) wrapped around the outside bottom of a small jointed tube which fits inside a larger jointed tube with a Pt foil cathode (30 cm$^2$) lining the inside (avg electrode gap=2.5 mm). Using a 30 amp DC power supply (Hewlett Packard Model No. 6269B), a constant current (current density 0.25 A/cm$^2$) of 5 amp was applied until 56,000 coulombs (1.2F/mol) were passed at which point complete conversion of hydroxy acid was indicated by gas chromatography. The reaction and gas evolution (H$_2$ and CO$_2$) proceed normally until ca. 1.0 F/mol current are passed, after which the resistance and solution pH are observed to increase. The colorless reaction mixture was then concentrated on a rotovap, and the resulting solid residue was extracted EtOAc (500 mL). After filtering, the remaining solids were stirred with EtOAc (100 mL) for 10 h, filtered, and the combined EtOAc extracts (600 mL) were concentrated to a colorless solid. The solids were dissolved in a minimum amount of warm Et$_2$O, quickly filtered through a coarse frit, and the filtrate cooled to −78° C. After two hours, the colorless crystals were filtered, washed with cold pentane, and dried in vacuo (Yield 14.4 g, 48%). mp 53° C.-54° C.; [α]$^{25}$D = −39.6°±0.5° (c 1, CHCl$_3$) $^1$H NMR (CD$_2$Cl$_2$)δ1.15 (d, J$_{HH}$=6.2 Hz, 6H, CH$_3$), 1.50 (m, 4H, CH$_2$), 2.95 (br, 2H, OH), 3.75 (m, 2H, CH); $^{13}$C NMR (CD$_2$Cl$_2$)δ23.6, 35.9, 68.1. Anal. Calcd for C$_6$H$_{14}$O$_2$: C, 60.98; H, 11.94. Found: C, 61.12; H, 11.64.

c) Preparation of (2S,5S)-2,5-hexanediol. Prepared as described above except that (3S)-3-hydroxybutyric acid was used as substrate. [α]$^{25}$D=+39.4°±0.5° (c 1, CHCl$_3$). Other spectroscopic properties were identical to those given for (R,R)-2a.

d) Preparation of (2R,5R)-2,5-hexanediol bis(methanesulfonate). To a solution of (2R,5R)-2,5-hexanediol (8.9 g, 0.075 mol) in CH$_2$Cl$_2$ (200 mL) was added triethylamine (26.2 mL, 0.188 mol). The solution was cooled to 0° C., and methanesulfonyl chloride (12.82 mL, 0.166 mol) in CH$_2$Cl$_2$ (30 mL) was added dropwise over 30 min. Upon complete addition, the mixture containing precipitated salts was allowed to stir at 0° C. for 30 min, and then at 25° C. for 30 min. The mixture was then poured into 1N HCl (250 mL) at 0° C. After shaking, the layers were separated and the aqueous layer was extracted with CH$_2$Cl$_2$ (2×50 mL). The combined organic layers were washed successively with 1N HCl (50 mL), saturated NaHCO$_3$, and brine. After drying (MgSO$_4$), the solution was concentrated on a rotovap to a pale yellow oil (18.2 g, 88%). The crude product thus obtained was sufficiently pure to be used in further reactions. $^1$H NMR (CDCl$_3$)δ1.41 (d, J$_{HH}$=6.3 Hz, 6H, CH$_3$), 1.78 (m, 4H, CH$_2$), 3.0 (s, 6H, CH$_3$), 4.85 (m, 2H, CH). The same general procedure was followed to prepare the other bis(methanesulfonates) used in this study.

e) Preparation of (2R,5R)-2,5-dimethyl-1-phenylphospholane. To a slurry of Li$_2$PPh.THF (20.3 g, 0.105 mol) in THF (300 mL) at −78° C. was added dropwise a solution of (2S,5S)-2,5-hexanediol bis(methanesulfonate) (26.0 g, 0.095 mol) in THF (50 mL). Upon complete addition, the orange mixture was allowed to stir at −78° C. for 1 h. The reaction was then slowly warmed to 25° C. and, after transferring to the glovebox, stirring was continued for 16 h. The resulting pale yellow mixture was filtered through a coarse frit, and concentrated to a semi-solid. Extraction with pentane (100 mL) and filtration, followed by concentration in vacuo yielded a pale yellow oil. Distillation afforded the product as a colorless oil (13.9 g, 76%): bp 61–64° C. (0.2 torr); [α]$^{25}$D=−51.0°±1° (c 1, hexane); $^1$H NMR (C$_6$D$_6$)δ0.70 (dd, J$_{HH}$=7.2 Hz, J$_{PH}$=10.6 Hz, 3H, CH$_3$), 1.1–1.3 (m, 2H, CH$_2$), 1 20 (dd, J$_{HH}$=7.2 Hz, J$_{PH}$=18.8 Hz, 3H, CH$_3$), 1.65 (m, 1H, CH), 2.0 (m, 2H, CH$_2$), 2.45 (m, 1H, CH); $^{31}$P NMR (C$_6$D$_6$)δ10.0; $^{13}$C NMR (C$_6$D$_6$) δ15.43 (CH$_3$), 21.23 (d, J$_{PC}$=34.2 Hz, CH$_3$), 32.25 (d, $^2$J$_{PC}$=10.0 Hz, CH$_2$), 35.62 (d, $^2$J$_{PC}$=13.1 Hz, CH$_2$), 37.17 (CH), 37.24 (d, J$_{PC}$=3.6 Hz, CH), 128.11, 128.30, 134.51 (d, J$_{PC}$=19.0 Hz, ortho), 137.67 (d, J$_{PC}$=28.1 Hz, ipso Ph); HRMS (EI, direct insert): m/z 192.1068 (M+, exact mass calcd for C$_{12}$H$_{17}$P: 192.1068), 177.0839 (M-CH$_3$), 150.0559 (M-C$_3$H$_6$), 135.0367 (M-C$_4$H$_9$), 108.0127 (C$_6$H$_5$P fragment).

f) Preparation of (2S, 5S)-2,5-dimethyl-1-phenylphospholane. This Compound was prepared from (2R,5R)-2,5-hexanediol bis(methanesulfonate) using the above procedure. [α]$^{25}$D = +51.6°±1° (c 1, hexane). Other spectroscopic properties identical to (R,R)-2a.

g) Preparation of Bis(2((2S, 5S)-2,5-dimenthylphospholanoethyl)phenylphosphine. To (2S,5S)-2,5-dimethyl-1-phenylphospholane (6.0 g, 0.031 mol) in THF (100 mL) at 25° C. under Ar was added clean Li ribbon (0.55 g, 0.079 mol), and the reaction was allowed to stir for 12 h. To the resulting brown/green mixture was added MeOH (1.64 mL, 0.04 mol, 1.3 equiv.) dropwise and the reaction warmed and a gelatinous precipitate (LiOMe) formed. After stirring for 10 min, a THF solution (10 mL) of divinylphenylphosphine (2.27 g, 0.14 mol) was added dropwise via pipet. The reaction remained warm, and after stirring for 30 min, MeOH (6 mL) was slowly added to the brown mixture to produce a pale yellow slurry. After 10 min, the reaction was filtered through a large (600 mL) medium porosity frit and the filtrate concentrated to a pale yellow oil. The resulting oil was dissolved in pentane (100 mL) and filtered. Concentration of the filtrate afforded a pale yellow oil which was distilled in vacuo to yield the product as a colorless oil (3.05 g, 55%): bp 73° C. -75° C. (0.025 torr); [α]$^{25}$D = -137°±4° (c 1, hexane); $^1$H NMR (C$_6$D$_6$)δ0.83 (dd, J$_{HH}$=7.17 Hz, J$_{PH}$=9.7 Hz, 3H, CH$_3$), 0.92 (dd, J$_{HH}$=7.15 Hz, J$_{PH}$=9.7 Hz, 3H, CH$_3$), 1.15 (dd, J$_{HH}$= 7.10 Hz, J$_{PH}$=11.6 Hz, 3H, CH$_3$), 0.9-1.40 (m, 5H, CH$_2$), 1.21 (dd, J$_{HH}$=7.17 Hz, J$_{PH}$=11.6 Hz, 3H, CH$_3$), 1.50-1.80 (m, 2H, CH, CH$_2$), 1.80-2.10 (m, 5H, CH, CH$_2$), 7.10 (m, 3H, Ph), 7.55 (m, 2H, Ph); $^{31}$P NMR (C$_6$D$_6$)δ-16.15 (dd, J$_{PP}$=24.0 Hz, 1P, Pph), 3.29 (d, J$_{PP}$=24.0 Hz, 1P), 3.48 (d, J$_{PP}$=24.0 Hz, 1P); $^{13}$C NMR (CDCl$_3$)δ14.23 (CH$_3$), 14.28 (CH$_3$), 19.05 (dd (overlapping), 2C, bridge CH$_2$), 21.03 (d, J$_{PC}$=29.5 Hz, CH$_3$), 21.06 (d, J$_{PC}$=28.8 Hz, CH$_3$), 24.47 (d, J$_{PC}$=15.5 Hz, CH$_2$), 24.67 (d, J$_{PC}$=15.7 Hz, CH$_2$), 34.02, 34.15, 36.65 (dd, J$_{PC}$=3.8 Hz), 36.99 (ring CH$_2$), 37.55 (d, J$_{PC}$=8.81 Hz, ring CH), 37.67 (d, J$_{PC}$=8.71 Hz, ring CH), 128.29, 128.38, 128.88, 132.39 (d, J$_{PC}$=18.5 Hz, ipso-Ph); HRMS (EI, direct insert): m/z 394.2107 (M+, exact mass calcd for C$_{22}$H$_{37}$P$_3$:394.2108), 279.1402 (M-C$_6$H$_{12}$P), 251.1110 (M-C$_8$H$_{16}$P).

EXAMPLE 2

Preparation of Bis(2-((2S, 5S)-2,5-dimethylphospholanoethyl))amine

To (2S,5S)-2,5-dimethyl-1-phenylphospholane (5.0 g, 0.026 mol) in THF (100 mL) at 25° C. under Ar was added clean Li ribbon (0.463 g, 0.067 mol), and the reaction was allowed to stir for 12 h. To the resulting brown/green mixture was added bis(2-chloroethyl)-trimethylsilylamine (2.62 g, 0.012 mol) in THF (5 mL) dropwise and the reaction was allowed to stir for 2 h. To the resulting mixture was then added MeOH (5 mL), and after 10 min, the colorless reaction was filtered through a large (600 mL) medium porosity frit and the filtrate concentrated to a pale yellow oil. The resulting oil was dissolved in pentane (100 mL) and filtered. Concentration of the filtrate afforded a pale yellow oil (2.91 g). To the resulting oil was added THF (25 mL), followed by n-Bu$_4$NF (9.4 mL of a 1M solution in THF), and the reaction was allowed to stir for 5 h. Concentration of the mixture afforded an orange residue which was extracted with pentane (50 mL) and filtered through a celite pad. Concentration of the filtrate provided the product as a pale yellow oil (2.23 g, 57%): [α]$^{25}$D = -157.6°±4° (c 1, hexane); $^1$H NMR (CDCl$_3$)δ1.06 (dd, J$_{HH}$=7.16 Hz, J$_{PH}$=9.8 Hz, 6H, CH$_3$), 29 (dd, J$_{HH}$=7.16 Hz, J$_{PH}$=17.75 Hz, 6H, CH$_3$), 0.90-1.40 (m, 7H, CH$_2$), 1.65 (m, 2H, CH, CH$_2$), 1.80 (m, 4H, CH, CH$_2$), 2.00 (m, 4H, CH, CH$_2$), 2.80 (m, 4H, CH, CH$_2$); $^{31}$P NMR (C$_6$D$_6$)δ-5.3; $^{13}$C NMR (C$_6$D$_6$)δ14.57 (CH$_3$), 21.39 (d, J$_{PC}$=31.0 Hz, CH$_3$), 25.05 (d, J$_{PC}$=22.0 Hz, bridge CH$_2$), 33.87 (d, J$_{PC}$=11.6 Hz, ring CH), 37.11 (d, J$_{PC}$=4.5 Hz, ring CH$_2$), 37.47 (ring CH$_2$), 38.40 (d, J$_{PC}$=10.9 Hz, ring CH), 48.04 (d, J$_{PC}$=22.0 Hz, bridge CH$_2$).

EXAMPLE 3

Preparation of Bis(2-((2S, 5S)-2,5-dimenthylpholanoethyl))ether

To (2S, 5S)-2,5-dimethyl-1-phenylphospholane (3.0 g, 0.016 mol) in THF (100 mL) at 25° C. under Ar was added clean Li ribbon (0.280 g, 0.040 mol), and the reaction was allowed to stir for 12 h. To the resulting brown/green mixture was added a THF solution (5 mL) of bis(2-chloroethyl)-ether (1.07 g, 7.5 mmol). After stirring for 1 h, MeOH (3 mL) was slowly added to the brown mixture to produce a colorless slurry. After 10 min, the reaction was filtered through a large (125 mL) medium porosity frit and the filtrate was concentrated to a pale yellow oil. The resulting oil was dissolved in pentane (100 mL) and filtered. Concentration of the filtrate afforded a pale yellow oil which was distilled in vacuo to yield the product as a colorless oil (0.53 g, 22%): bp 62° C.-63° C.(0.06 torr); [α]$^{25}$D = -132.0°±4° (c 1, hexane); $^1$H NMR (C$_6$D$_6$)δ0.91 (dd, J$_{HH}$=7.12 Hz, J$_{PH}$=10.0 Hz, 3H, CH$_3$),1.13 (dd, J$_{HH}$=7.15 Hz, J$_{PH}$=18.0 Hz, 6H, CH$_3$), 0.97 (m, 2H, CH$_2$), 1.15 (m, 2H, CH$_2$), 1.33 (m, 2H, CH$_2$), 1.55 (m, 2H, CH$_2$), 1.70 (m, 3H, CH, CH$_2$), 1.85 (m, 3H, CH, CH$_2$), 2.05 (br, 2H, CH$_2$), 3.60 (m, 4H, CH$_2$O); $^{31}$P NMR (C$_6$D$_6$)δ-8.3; $^{13}$C NMR (C$_6$D$_6$)δ14.53 (CH$_3$), 21.15 (d, J$_{PC}$=30.9 Hz, CH$_3$), 27.99 (d, J$_{PC}$=22.0 Hz, CH$_2$), 33.61 (d, J$_{PC}$=10.7 Hz, CH$_3$), 37.08 (d, J$_{PC}$=4.6 Hz, CH), 37.39, 38.31 (d, J$_{PC}$=9.9 Hz, CH$_2$), 60.98 (d, J$_{PC}$=25.6 Hz, CH$_2$O); HRMS (EI, direct insert): m/z 302.1900 (M+, exact mass calcd for C$_{16}$H$_{32}$OP$_2$:302.1929), 187.1232 (M-C$_6$H$_{12}$P), 160.0947 (MC$_8$H$_{15}$P).

EXAMPLE 4

Preparation of [(COD)Rh(Bis(2-((2S, 5S)2,5-dimethylphospholanoethyl))amine)]+SbF$_6$−

To [(COD)$_2$Rh]+SbF$_6$−(0.50 g, 0.9 mmol) slurried in THF (15 mL) was added a THF solution (5 mL) of bis(2((2S,5S)-2,5-dimethylphospholanoethyl))amine (0.30 g, 1.0 mmol). The solution became homogeneous and orange/yellow in color upon addition. After 20 min, Et$_2$O (25 mL) was slowly added to precipitate the product as a pale orange solid which was filtered, washed with Et$_2$O (2×10 mL) and dried. Recrystallization from CH$_2$Cl$_2$/Et$_2$O afforded the title complex as an orange crystalline solid (0.41 g, 61%).

1H NMR (CD$_2$Cl$_2$)δ0.92 (dd, J$_{HH}$=7.5 Hz, J$_{PH}$=17.5 Hz, 3H, CH$_3$), 1.10 (dd, J$_{HH}$=6.9 Hz, J$_{PH}$=12.7 Hz, 3H, CH$_3$), 1.48 (dd, J$_{HH}$=7.2 Hz, J$_{PH}$=13.6 Hz, 3H, CH$_3$), 1.59 (dd, J$_{HH}$=7.3 Hz, J$_{PH}$=16.1 Hz, 6H, CH$_3$),1.25–1.70 (m, 4H), 1.7–2.0 (m, 4H), 2.0–2.5 (m, 12H), 2.55–2.8 (m, 4H), 2.8–3.0 (m, 4H), 3.42 (br, 1H, NH), 3.60 (br, 4H, COD-CH); $^{31}$P NMR (CD$_2$Cl$_2$)δ50.63 (dd, J$_{RhP}$= 106.2 Hz, J$_{PP}$=29.9 Hz), 62.74 (dd, J$_{RhP}$=113.9 Hz, J$_{PP}$=29.9 Hz)

EXAMPLE 5

Preparation of [Rh(Bis(2-((2S, 5S)-2,5-dimenthylphospholanoethyl))phosphine(Cl]

To [(COD)RhCl]$_2$ (0.062 g, 0.126 mmol) in THF (5 mL) was added a THF solution of bis(2-((2S,5S)-2,5dimethylphospholanoethyl))phenylphosphine (0.1 g, 0.252 mol). The solution turned yellow and homogeneous upon addition. After stirring for 30 min, the solution was concentrated to 3 mL and hexanes added to precipitate a pale yellow microcrystalline solid. Recrystallization from THF/hexane afforded the pale yellow crystalline product (0.110 g, 81%): $^1$H NMR (THF-d$_8$)δ1.0 (m, 6H, CH$_3$), 1.15 (m, 6H, CH$_3$),1.2–1.4 (m, 8H), 1.55 (m, 4H), 1.7–2.2 (m 4H) 2.4 (m 2H), 2.75 (m, 2H), 1.73 (m, 2H, Ph), 8.0 (m, 3H, Ph); $^{31}$P NMR (THF-d$_8$)δ67.35 (ddd, J$_{RhP}$=139.8 Hz, J$_{PP}$=26.3 Hz, J$_{PP}$=29.3 Hz, 2P coincidental overlap), 115.70 (ddd, J$_{RhP}$=167.9 Hz, J$_{PP}$=29.3 Hz, J$_{PP}$=29.3 Hz, 1P--central P).

What is claimed is:

1. A compound represented by the following formula comprising:

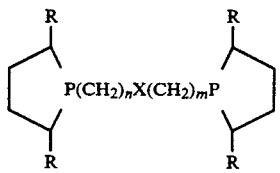

wherein:
X is O, S, NR", PR", AsR", SbR", divalent aryl, divalent fused aryl, divalent 6-membered ring heterocyclic group, divalent 5-membered ring heterocyclic group, or divalent fused heterocyclic group, wherein R" is hydrogen, C$_1$–C$_8$ alkyl, C$_1$–C$_8$ fluoroalkyl or C$_1$–C$_8$ perfluoroalkyl, aryl, substituted aryl, aralkyl, ring-substituted aralkyl, or CR'$_2$(CR'$_2$)$_q$Z(CR'$_2$)$_p$R' wherein Z is O, S, NR', PR', AsR', or SbR';

q and p are each integers, the same or different, ranging from 1 to about 8; and R' is H, F, aryl, C$_1$–C$_8$ alkyl, C$_1$–C$_8$ fluoroalkyl, or C$_1$–C$_8$ perfluoroalkyl;

n and m are each integers, the same or different, ranging from 1 to about 8; and R is a radical comprising C$_1$–C$_8$ alkyl, C$_1$–C$_8$ fluoroalkyl or C$_1$–C$_8$ perfluoroalkyl, aryl, substituted aryl, aralkyl, ring-substituted aralkyl, or—CR'$_2$(CR'$_2$)$_q$X(CR'$_2$)$_p$R' wherein q and p are each integers, the same or different, ranging from 1 to about 8;

R' is H, F, aryl, C$_1$–C$_8$ alkyl, C$_1$–C$_8$ fluoroalkyl or C$_1$–C$_8$ perfluoroalkyl; and X is O, S, NR", PR", AsR", SbR", divalent aryl, divalent fused aryl, divalent 6-membered ring heterocyclic group, divalent 5-membered ring heterocyclic group, or divalent fused heterocyclic group, wherein R" is hydrogen, C$_1$–C$_8$ alkyl, C$_1$–C$_8$ fluoroalkyl, C$_1$–C$_8$ perfluoroalkyl, aryl, substituted aryl, aralkyl, ring-substituted aralkyl, or CR'$_2$(CR'$_2$)$_q$Z(CR'$_2$)$_p$R' wherein Z is O, S, NR', PR', AsR', or SbR';

q and p are each integers, the same or different, ranging from 1 to about 8; and R' is H, F, aryl, C$_1$–C$_8$ alkyl, C$_1$–C$_8$ fluoroalkyl, or C$_1$–C$_8$ perfluoroalkyl.

2. The compound of claim 1 having a high degree of enantiomeric purity.

3. The compound of claim 1 which is a bis(trans-2,5disubstituted phospholane).

4. The compound of claim 3 wherein R is a C$_1$ to C$_6$ alkyl group.

5. The compound of claim 4 wherein n and m are each independently 1 to 3.

6. The compound of claim 5 wherein X is NH, O, or P-phenyl.

7. The compound of claim 4 wherein R is methyl.

8. The compound of claim 7 wherein n and m are each 2.

9. The compound of claim 8 wherein X is NH, O, or P-phenyl.

10. The compound of claim 1 which is bis(2-((2S,5S)-2,5-dimethylphospholanoethyl))phenylphosphine.

11. The compound of claim 1 which is bis(2-((2S,5S)-2,5-dimethylphospholanoethyl))amine.

12. The compound of claim 1 which is bis(2-((2S,5S)-2,5dimethylphospholanoethyl))ether.

13. The compound of claim 1 which is bis(2-((2R,5R)-2,5-dimethylphospholanoethyl))phenylphosphine.

14. The compound of claim 1 which is bis(2-((2R,5R)-2,5-dimethylphospholanoethyl))amine.

15. The compound of claim 1 which is bis(2-((2R,5R)-2,5-dimethylphospholanoethyl))ether.

16. A process for the preparation of a compound represented by the following formula:

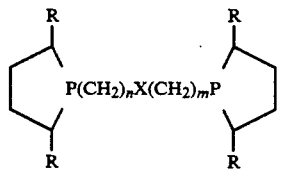

wherein:
X is O, S, NR", PR", AsR", SbR", divalent aryl, divalent fused aryl, divalent 6-membered ring heterocyclic group, divalent 5-membered ring heterocyclic group, or divalent fused heterocyclic group, wherein R" is hydrogen, C$_1$–C$_8$ alkyl, C$_1$–C$_8$ fluoroalkyl or C$_1$–C$_8$ perfluoroalkyl, aryl, substituted aryl, aralkyl, ring-substituted aralkyl, or CR'$_2$, (CR'$_2$)$_q$Z(CR'$_2$)$_p$R' wherein Z is O, S, NR', PR', AsR', or SbR';

q and p are each integers, the same or different, ranging from 1 to about 8; and R' is H, F, aryl, C$_1$–C$_8$ alkyl, C$_1$–C$_8$ fluoroalkyl, or C$_1$–C$_8$ perfluoroalkyl;

n and m are each integers, the same or different, ranging from 1 to about 8; and R is a radical comprising C$_1$–C$_8$ alkyl, C$_1$–C$_8$ fluoroalkyl or C$_1$–C$_8$ perfluoroalkyl, aryl, substituted aryl, aralkyl, ring-substituted aralkyl, or —CR′₂(CR′₂)$_q$X(CR′₂)$_p$R′ wherein q and p are each integers, the same or different, ranging from 1 to about 8.

R′ is H, F, aryl, C₁-C₈ alkyl, C₁-C₈ fluoroalkyl or C₁-C₈ perfluoroalkyl; and

X is O, S, NR″, PR″, AsR″, SbR″, divalent aryl, divalent fused aryl, divalent 6-membered ring heterocyclic group, divalent 5-membered ring heterocyclic group, or divalent fused heterocyclic group, wherein R″ is hydrogen, C₁-C₈ alkyl, C₁-C₈ fluoroalkyl, C₁-C₈ perfluoroalkyl, aryl, substituted aryl, aralkyl, ring-substituted aralkyl, or CR′₂(CR′₂)$_q$Z(CR′₂)$_p$R′ wherein Z is O, S, NR′, PR′, AsR′, or SbR′;

q and p are each integers, the same or different, ranging from 1 to about 8; and R′ is H, F, aryl, C₁-C₈ alkyl, C₁-C₈ fluoroalkyl, or C₁-C₈ perfluoroalkyl;

comprising reacting an optically active trans-2,5-disubstituted lithium phospholanide with a compound of the structure Y(CH₂)$_n$X(CH₂)$_m$Y wherein X, n and m are defined as above, and Y is a leaving group, to yield the desired compound as defined above.

17. The process of claim 16 conducted at a temperature of from about −78° C. to about 40° C.

18. The process of claim 16 conducted in tetrahydrofuran.

19. The process of claim 16 conducted in an inert atmosphere.

20. The process of claim 16 wherein the 2,5-disubstituted lithium phospholanide is a compound of the formula:

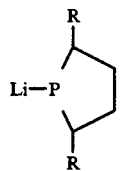

wherein:

R is a radical comprising C₁-C₈ alkyl, C₁-C₈ fluoroalkyl or C₁-C₈ perfluoroalkyl, aryl, substituted aryl, aralkyl, ring-substituted aralkyl, or —CR′₂(CR′₂(CR′₂)$_q$X(CR′₂)$_p$R′ wherein q and p are each integers, the same or different, ranging from 1 to about 8;

R′ is H, F, aryl, C₁-C₈ alkyl, C₁-C₈ fluoroalkyl or C₁-C₈ perfluoroalkyl; and

X is O, S, NR″, PR″, AsR″, SbR″, divalent aryl, divalent fused aryl, divalent 6-membered ring heterocyclic group, divalent 5-membered ring heterocyclic group, or divalent fused heterocyclic group, wherein R″ is hydrogen, C₁-C₈ alkyl, C₁-C₈ fluoroalkyl, C₁-C₈ perfluoroalkyl, aryl, substituted aryl, aralkyl, ring-substituted aralkyl, or CR′₂(CR′₂)$_q$Z(CR′₂)$_p$R′ wherein Z is O, S, NR′, PR′, AsR′, or SbR′;

q and p are each integers, the same or different, ranging from 1 to about 8; and R′ is H, F, aryl, C₁-C₈ alkyl, C₁-C₈ fluoroalkyl, or C₁-C₈ perfluoroalkyl.

21. A process for the preparation of a compound represented by the following formula:

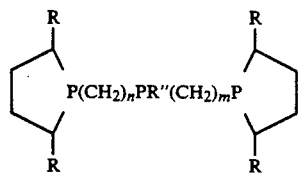

wherein:

R″ is hydrogen, C₁-C₈ alkyl, C₁-C₈ fluoroalkyl or C₁-C₈ perfluoroalkyl, aryl, substituted aryl, aralkyl, ring-substituted aralkyl, or CR′₂(CR′₂)$_q$Z(CR′₂)$_p$R′ wherein Z is O, S, NR′, PR′, AsR′, or SbR′;

q and p are each integers, the same or different, ranging from 1 to about 8; and R′ is H, F, aryl, C₁-C₈ alkyl, C₁-C₈ fluoroalkyl, or C₁-C₈ perfluoroalkyl;

n and m are each integers, the same or different, ranging from 1 to about 8; and R is a radical comprising C₁-C₈ alkyl, C₁-C₈ fluoroalkyl or C₁-C₈ perfluoroalkyl, aryl, substituted aryl, aralkyl, ring-substituted aralkyl, or —CR′₂(CR′₂)$_q$X(CR′₂)$_p$R′ wherein q and p are each integers, the same or different, ranging from 1 to about 8;

R′ is H, F, aryl, C₁-C₈ alkyl, C₁-C₈ fluoroalkyl or C₁-C₈ perfluoroalkyl; and

X is O, S, NR″, PR″, AsR″, SbR″, divalent aryl, divalent fused aryl, divalent 6-membered ring heterocyclic group, divalent 5-membered ring heterocyclic group, or divalent fused heterocyclic group, wherein R″ is hydrogen, C₁-C₈ alkyl, C₁-C₈ fluoroalkyl, C₁-C₈ perfluoroalkyl, aryl, substituted aryl, aralkyl, ring-substituted aralkyl, or CR′₂(CR′₂)$_q$Z(CR′₂)$_p$R′ wherein Z is O, S, NR′, PR′, AsR′, or SbR′;

q and p are each integers, the same or different, ranging from 1 to about 8; and R′ is H, F, aryl, C₁-C₈ alkyl, C₁-C₈ fluoroalkyl, or C₁-C₈ perfluoroalkyl, comprising reacting an optically active trans-2,5-disubstituted lithium phospholanide with a divinylphosphine of formula R″P(CH=CH₂)₂ wherein R″ is defined as above.

22. The process of claim 21 conducted at a temperature of from about −78° C. to about 40° C.

23. The process of claim 21 conducted in tetrahydrofuran.

24. The process of claim 21 conducted in an inert atmosphere.

25. The process of claim 21 wherein R″ is phenyl.

26. The process of claim 21 wherein the 2,5-disubstituted lithium phospholanide is a compound of the formula:

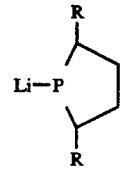

wherein:

R is a radical comprising C₁-C₈ alkyl, C₁-C₈ fluoroalkyl or C₁-C₈ perfluoroalkyl, aryl, substituted aryl, aralkyl, ring-substituted aralkyl, or —CR′$_2$(CR′$_2$)$_q$X(CR′$_2$)$_p$R′ wherein q and p are each integers, the same or different, ranging from 1 to about 8;

R′ is H, F, aryl, C$_1$–C$_8$ alkyl, C$_1$–C$_8$ fluoroalkyl or C$_1$–C$_8$ perfluoroalkyl; and X is O, S, NR″, PR″, AsR″, SbR″, divalent aryl, divalent fused aryl, divalent 6-membered ring heterocyclic group, divalent 5-membered ring heterocyclic group, or divalent fused heterocyclic group, wherein R″ is hydrogen, C$_1$–C$_8$ alkyl, C$_1$–C$_8$ fluoroalkyl, C$_1$–C$_8$ perfluoroalkyl, aryl, substituted aryl, aralkyl, ring-substituted aralkyl, or CR′$_2$(CR′$_2$)$_q$Z(CR′$_2$)$_p$R′ wherein Z is O, S, NR′, PR′, AsR′, or SbR′;

q and p are each integers, the same or different, ranging from 1 to about 8; and R′ is H, F, aryl, C$_1$–C$_8$ alkyl, C$_1$–C$_8$ fluoroalkyl, or C$_1$–C$_8$ perfluoroalkyl.

* * * * *